United States Patent [19]

Beckett

[11] Patent Number: 4,875,855

[45] Date of Patent: Oct. 24, 1989

[54] TOOL

[76] Inventor: David Beckett, 27 Erleigh Road, Reading RG1 5LU, Berkshire, England

[21] Appl. No.: 123,888

[22] Filed: Nov. 23, 1987

[30] Foreign Application Priority Data

Nov. 25, 1986 [GB] United Kingdom ............ 8628091

[51] Int. Cl.$^4$ .............................................. A61G 7/00
[52] U.S. Cl. ................................................... 433/3
[58] Field of Search .................... 140/118, 119, 120; 433/2, 3

[56] References Cited

U.S. PATENT DOCUMENTS

| | | | |
|---|---|---|---|
| 2,532,200 | 11/1950 | Smith | 433/3 |
| 3,596,357 | 8/1971 | Matsumoto | 433/3 |
| 3,759,302 | 9/1973 | Attenborough | 433/3 |
| 3,861,045 | 1/1975 | Canter et al. | 433/3 |
| 4,602,635 | 7/1986 | Mulhollan et al. | 128/354 R |

FOREIGN PATENT DOCUMENTS 1150999 5/1969 United Kingdom .

Primary Examiner—Robert Peshock
Attorney, Agent, or Firm—Andrus, Sceales, Starke & Sawall

[57] ABSTRACT

An orthodontic instrument for tightening a loop in a dental ligature about an anchor affixed to a tooth, to tie an archwire to the anchor, comprises a shaft having at one end a nose for bracing the tool against the wires and bracket; a movable ligature carriage on the shaft; and means on the carriage to hold a dental ligature to the carriage with a loop in the ligature projecting around and beyond the nose of the shaft. The ligature carriage is movable along the shaft to draw the ligature loop towards the abutment at the nose of the shaft and tighten the loop before twisting the ligature 180°, to seat the archwire in the anchor on the tooth, and then spinning the shaft to twist the wires.

11 Claims, 5 Drawing Sheets

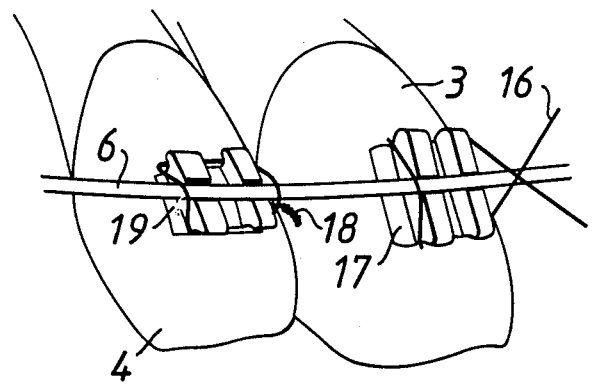
FIG.1.
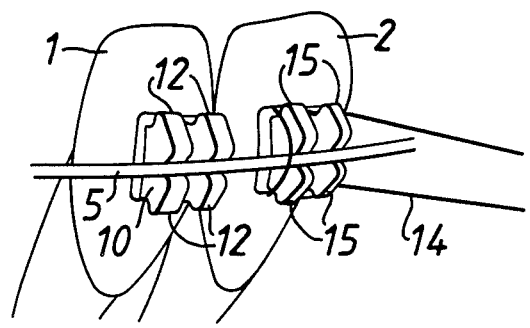
FIG.2(a)
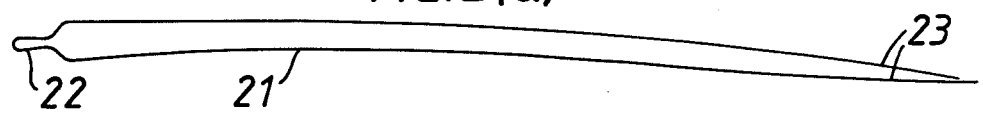
FIG.2(b)
FIG.2(c)
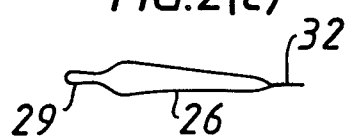
FIG.2(d)
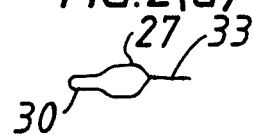

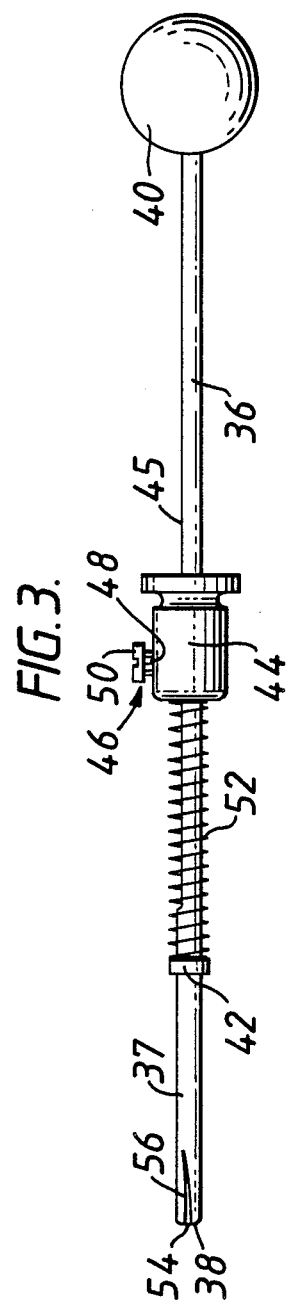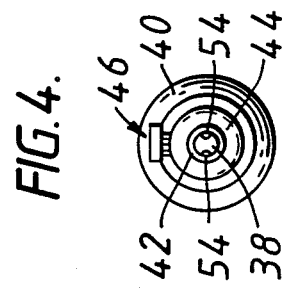
FIG.3.
FIG.4.

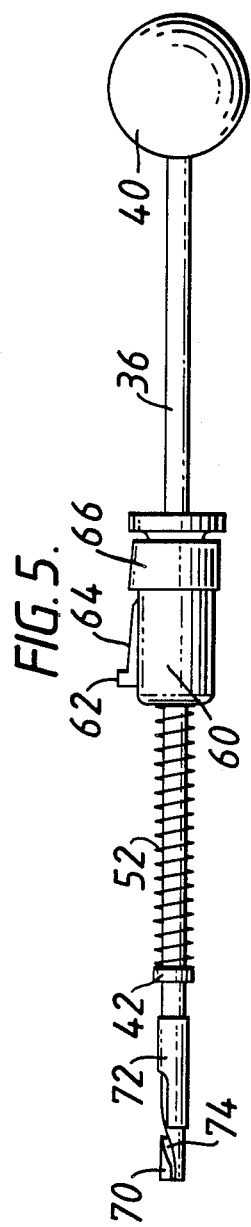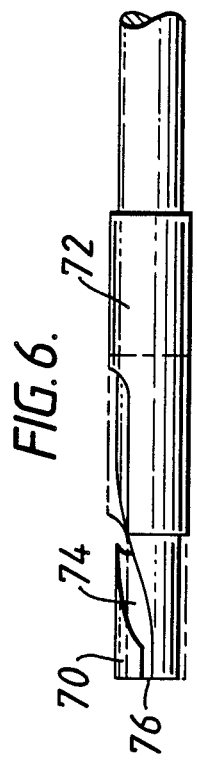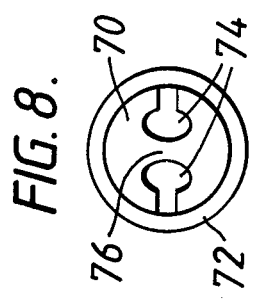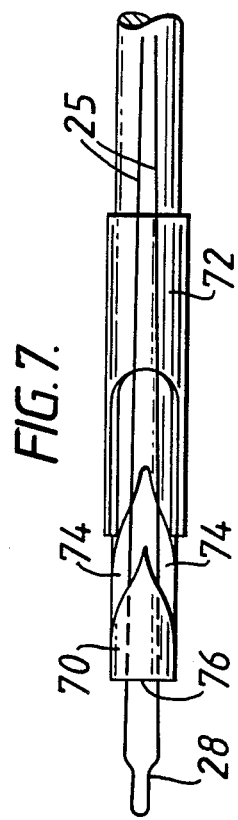

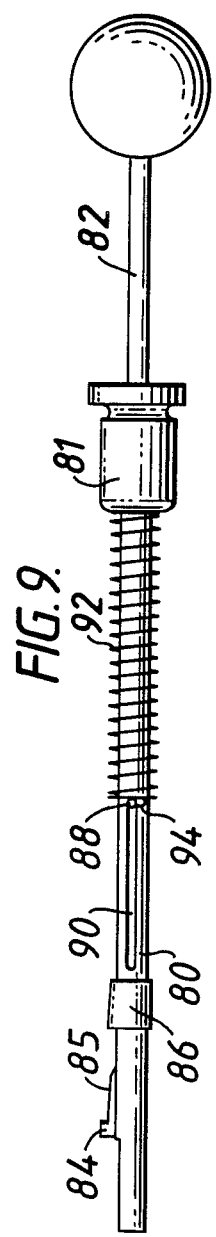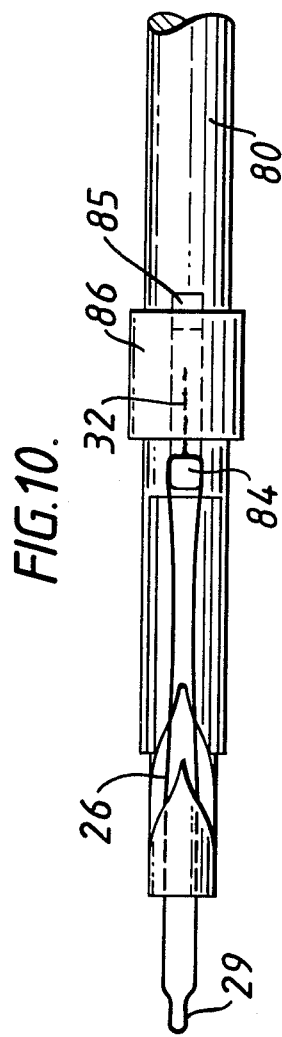

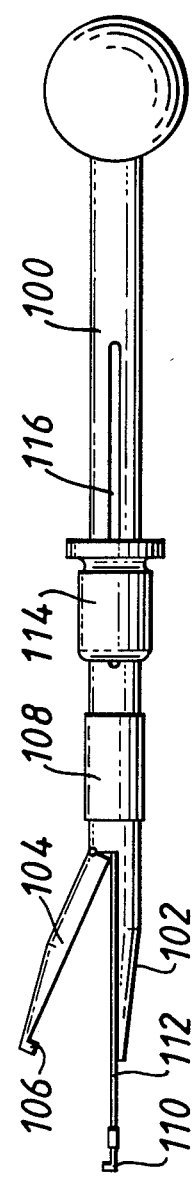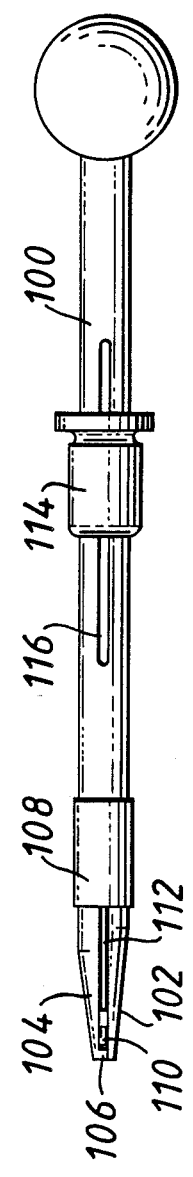

TOOL

This invention relates to a tool, and in particular to a tool for tightening a loop in a dental ligature about an anchor affixed to a tooth.

In orthodontic dentistry, it is from time to time necessary to attach an archwire to a tooth or teeth. This is normally achieved indirectly by securing a bracket to the tooth, typically by cementing or bonding the bracket to the labial surface of the tooth, and subsequently fastening the archwire to the bracket, typically by tightening a stainless steel ligature wire around the bracket and over the archwire. The bracket forms an anchor on the tooth for the archwire.

The tool provided by the present invention may be adapted for use as an effective instrument for tightening the ligature wire around a bracket, after looping the ligature wire around the bracket and an archwire, by twisting the ligature wire.

The ligature wire may have free ends, or may be preformed in a large loop with the ends of the wire already twisted or otherwise held together.

Tools currently available for this purpose include pliers for holding and stretching the ligature wires apart while the pliers are rotated by hand to twist the wire and seat the archwire on the bracket, and tools for simply holding a preformed ligature loop while it is twisted. Variations in wire tension may easily occur during the twisting operation, and the bracket may even be pulled off the tooth.

One object of the present invention is to provide an improved orthodontic instrument for tying a dental ligature.

According to one aspect of the present invention a tool for tightening a loop in a dental ligature about an anchor affixed to a tooth comprises a shaft having at one end a nose terminating in an abutment; a ligature carriage carried by the shaft; and ligature mounting means on the carriage adapted to hold a dental ligature to the carriage with a loop in the ligature projecting around and beyond the abutment at the nose of the shaft; the ligature carriage being movable longitudinally of the shaft whereby, in use, to draw the loop towards the abutment at the nose of the shaft and nip a said anchor in the loop between the ligature and the abutment.

In use, as will later be described in more detail with reference to the drawings, a ligature is mounted on the carriage with a loop extending beyond the nose of the tool. The anchor is normally a bracket with a seat for the archwire. The loop is hooked over lugs on the bracket on either side of the archwire. The carriage is then drawn by the operator along the shaft away from the nose of the tool, shortening the exposed ligature loop, until the abutment meets the bracket and archwire. The tension in the loop around the bracket is maintained within the tool, and not by pulling against the bracket. The shaft is then rotated to twist the ligature and seat the archwire on the bracket.

On rotation of the shaft, the ligature rotates as the abutment rotates. It may be preferred also to secure the ligature carriage against free rotation, relative to the shaft, about the shaft axis. This may be achieved by providing a non-circular aperture through the carriage and passing a portion of the shaft of corresponding cross section through the aperture in the carriage. The carriage may alternatively be slidably keyed to the shaft by other means.

In order to provide a tension bias in the ligature loop, it may also be advantageous to provide the tool with spring means adapted to urge the carriage away from the nose of the shaft. The spring means suitably comprises a coil spring around or within the shaft, acting between the carriage and reaction means secured to the shaft.

The nose of the tool is advantageously provided with locating means for guiding the loop with respect to the nose of the shaft during movement of the carriage. The locating means may comprise peripheral notches, grooves or channels in the nose of the shaft. Such locating means are preferably evenly spaced about the end of the shaft in order to draw the strands of the ligature apart to the fullest extent prior to and during twisting.

Latch means may be provided to allow insertion of the strands of the ligature into the locating means but prevent their accidental displacement therefrom. Suitable latch means comprises a sleeve on the shaft adjacent the nose thereof, the sleeve being alternately movable away from the nose to expose the channels at the sides of the nose to enable a ligature to be placed in or removed from the channels, and movable towards the nose to cover the channels and retain a ligature therein. The sleeve may be lockable in position when covering the channels.

In an embodiment of the invention suitable for use with small pre-formed ligatures, the shaft is hollow, the nose of the shaft is openable, the ligature mounting carriage is carried within the shaft and is movable out of the nose when the nose is open to permit loading a ligature thereon, and means for moving the carriage is provided externally of the shaft.

The openable nose may comprise a segment thereof hinged to the shaft, and a locking collar provided on the shaft which is slidable along the shaft to overlie the segment and retain it closed.

The ligature mounting means on the carriage may take a variety of forms. Simple mounting means may for example comprise a stud or post over which one end of a ligature loop can be hooked, or about which loose strands of a ligature can be wound, or one or more tapered slots adapted to grip strands pulled into the slots, or combinations of these or other means. Preferred mounting means comprise an upstanding post, a ramp adjacent the post extending downwardly from the post away from the nose of the tool, and clamp means over the ramp movable towards the post whereby to entrap strands of a ligature, which, in use, pass from the nose of the tool past either side of the post and on to the ramp, between the clamp means and the ramp.

Preferably the shaft is substantially straight, at least from the nose to the limit of normal travel of the carriage away from that end. Handle means may be provided at the end of the shaft opposite the nose.

Some embodiments of tools in accordance with the invention, being orthodontic instruments, are illustrated, by way of example only, in the accompanying drawings, in which:

FIG. 1 illustrates stages in the location and tightening of a ligature loop around an archwire and a bracket affixed to the labial surface of a tooth;

FIGS. 2(a)–(d) show four ligatures for use with the illustrated embodiments of the invention;

FIG. 3 is a side elevation of a first tool according to the invention;

FIG. 4 is an end elevation of the tool of FIG. 3;

FIG. 5 is a side elevation of a second tool;

FIG. 6 is an enlarged detail showing the nose of the second tool;

FIG. 7 is a plan view of the detail shown in FIG. 6;

FIG. 8 is an end elevation of the detail shown in FIGS. 6 and 7;

FIG. 9 is a side elevation of a third tool;

FIG. 10 is an enlarged detail showing the nose of the third tool in plan;

FIG. 11 is a side elevation of a fourth tool, open for loading; and

FIG. 12 is a side elevation of the fourth tool closed.

FIG. 1 shows two adjacent lower teeth 1, 2 and two adjacent upper teeth 3, 4. Lower archwire 5 and upper archwire 6 are to be secured to the teeth. For the purpose of illustration, each tooth is shown at a different stage of the securing process.

Tooth 1 illustrates a first stage in which a bracket 10 has been affixed to the labial surface of the tooth. The bracket has seat portions 11 for the archwire 5, and lugs 12 on either side of the archwire seat.

At tooth 2 a loop of ligature wire 14 has been hooked behind lugs 15 but passes over the archwire 5. At tooth 3, ligature wires 16 have now been crossed over archwire 6. Further twisting of the wires will first seat the archwire in bracket 17, then tighten the ligature.

The completed tie is shown at tooth 4, ligature wires 18 have been twisted tight and archwire 6 is well seated on bracket 19. The ends of the ligature wire have been cut off.

FIG. 2(a) shows a stainless steel ligature wire 21 for use with the first tool illustrated in FIGS. 3 and 4. It is bent into a large loop with a narrow nose loop portion 22 for binding an archwire to a bracket, and has two free cut ends 23.

FIGS. 2(b), 2(c) and 2(d) show further ligature loops 25, 26 and 27 for use with the second, third and fourth tools respectively. These ligatures have similar narrow nose loop portions 28, 29 and 30 but they differ in length and their cut ends 31, 32 and 33 are already twisted together.

The first tool shown in FIGS. 3 and 4 comprises a straight shaft 36 formed from a round steel rod. The shaft has a nose 37 terminating in an abutment 38 at one end and a handle 40 moulded on to the opposite end of the shaft.

A collar 42 is fixed to the shaft a short distance from the nose. A flat land 45 on the shaft, from the handle to a point on the handle side of the collar, gives this portion of the shaft a non-circular section.

A ligature carriage 44 is slidably mounted on the non-circular portion of the shaft, which passes through a corresponding aperture in the carriage. The carriage is thereby secured against rotation on the shaft. Ligature mounting means on the carriage comprises a stud 46 with a serrated shank 48 and an enlarged slotted head 50.

A light compression spring 52 is mounted on the shaft between the collar and the carriage. The collar provides reaction means for the spring, and acts as a stop for one end of the spring to enable the spring to urge the carriage away from the nose of the shaft when the carriage abuts the compressed spring.

The nose of the shaft is provided with locating means for the ligature loop in the torn of two diametrically opposed peripheral notches 54 which taper as grooves or channels 56 along the sides of the shaft in general alignment with the ligature mounting means on the carriage.

To use the tool to secure an archwire to a bracket affixed to a tooth in a patient's mouth, the sequence shown in FIG. 1 is followed. A ligature wire as shown in FIG. 2(a) is positioned with the nose loop portion 22 around the bracket, and the two free ends 23 are crossed over the archwire. The tool is held in one hand by the handle 40, and the carriage 44 is slid by the thumb and forefinger away from the handle to compress the spring 52.

The abutment 38 at the nose of the tool is then placed against the crossed wires on the bracket. The free ends of the wires are drawn back by hand to locate the wires in the notches 54 and grooves 56, and the wires are then wrapped around the serrated shank 48 of the stud 46 and finally into the slot in the head 50 to secure the wires to the carriage.

The ligature wires are then tightened by drawing the carriage back towards the handle between finger and thumb, to nip the archwire and the bracket in the ligature nose loop against the abutment 38. The abutment remains in contact with the ligature/archwire/bracket assembly on the tooth, thus bracing the shaft and ensuring no displacement at the tooth. Maintaining the pressure, the tool is rotated through a further quarter turn to twist the ligature and seat the archwire into the bracket.

The thumb and forefinger grip on the carriage can then be released and the tool spun by rotating the shaft between thumb and forefinger between the carriage and the handle. The wires are rapidly and evenly wrapped around one another. As the ends of the wires become shorter, the carriage is drawn down the shaft against the substantially constant pressure of the compressed spring, maintaining a steady tension in the wires.

When the wires are sufficiently twisted, the ends are released from the carriage, enabling the tool to be set aside. The excess ligature wire is then cut off in the normal manner and discarded.

The second tool shown in FIGS. 5 to 8 is generally similar except for the ligature mounting means on the carriage 60, and in the detail of he nose 70 of the tool. Unchanged features have the same reference numerals as in FIGS. 3 and 4.

The modified nose 70 of the tool is best seen in FIGS. 6 to 8. Locating means for guiding the ligature loop are provided by two deep, oval section channels 74 extending back on opposite sides of the nose on either side of abutment 76, and inclining towards the top of the shaft 36 (as shown). A sliding sleeve 72 is movable on the nose to cover or uncover the channels 74 at the sides of the shaft, the top of the sleeve being cut away at the nose end to allow the ligature wires to emerge from the channels and extend unrestrictedly towards the ligature carriage 60.

The modified ligature carriage 60 is again mounted slidably and nonrotatably on the shaft 36, but is formed with ligature mounting means comprising an upstanding post 62, a ramp 64 adjacent the post extending downwardly away from the nose of the tool, and a clamping ring 66 around the carriage which is slidable on the carriage over the ramp towards the post. To load a ligature thereon, the twisted ends 31 of a preformed ligature 25 (FIG. 2(b)) are hooked over the post and laid on the ramp before the ring 66 is slid towards the post to clamp the ligature ends 31 thereon.

This mounting means uses little wire, can be used for ligature wires of different thicknesses, and keeps the sharp cut ends of the wire covered.

This second tool is loaded in a generally similar way to the first, except that the sleeve 72 is slid back to the position shown in the drawings, to expose the channels 74, before loading the ligature at the nose of the tool. The sleeve is then closed over the channels, to the position shown in phantom in FIG. 6, to retain the ligature therein before the twisted ends of the ligature are fastened to the carriage. This is preferably done before applying the ligature to the bracket.

This tool can be used to make a series of ties with one ligature. After tightening the narrow ligature nose loop 28 around a first archwire and bracket, as described for the first tool, twisting may be continued towards a second bracket. Shortly before the second bracket is reached, the tool can be pulled by the handle to expose new untwisted ligature wires. These can be guided around the next bracket and the tightening process continued, and repeated for further brackets on the arch. After making the last tie the ligature is cut in the usual way, and the tool can be reloaded if required.

The deep channels 74 protect the nose of the tool from undue wear between the channels and the sleeve, as further wire is paid out.

The third tool is shown in FIGS. 9 and 10. This uses the shorter ligatures 26 shown in FIG. 2(c), which are loaded into the tool before use (FIG. 10). It differs from the second tool principally in that the ligature carriage 60 and sleeve 72 (FIG. 5) are now made in one piece as sleeve 80, extending back to and carrying a finger grip 81. Ligature mounting means comprising a post 84, a ramp 85 and a sliding clamping ring 86 function as in the second tool but are located on the sleeve much close to the nose of the tool.

The shaft 82 can be circular. The sleeve and ligature carriage 80 is now prevented from rotating on the shaft by pin 88 extending through the shaft and lying in longitudinal slots 90 in opposite sides of the sleeve. Pin 88 also serves as the reaction means for one end of spring 92.

The handle end of each slot has a lateral notch 94 which enables the sleeve 80 to be locked against the compressed spring by making a small rotation of the sleeve to engage pin 88 in the notches 94. The length of the slot limits the movement of the sleeve, and in the locked position the sleeve exactly covers the nose of the tool with sufficient ligature loop exposed to permit easy initial positioning of the ligature loop around a bracket on a tooth, before unlocking the sleeve.

The fourth tool shown in FIGS. 11 and 12 is for use with the smallest ligatures 27 (FIG. 2(d)). This tool has a hollow shaft 100 with a tapered nose 102. One half-segment of the nose is formed as an openable upper jaw 104 hinged to the shaft and terminates in a short round abutment stud 106 which, when the jaw is closed, lies against the fixed lower jaw of the nose. Locking collar 108 is slidable on the shaft between a rearward position (FIG. 11) in which the jaw 104 can be opened, and a forward position (FIG. 12) in the which the jaw 104 is held closed.

Ligature mounting means 110, comprising a post, ramp and clamping ring as previously described but of smaller overall dimensions, are mounted on a ligature carriage comprising a rod 112 mounted axially within the hollow shaft. The rod is connected through slot 116 to a finger grip ring 114 which slides along the outside of the shaft. Optionally, spring means are provided in the shaft to bias the ligature carriage away from the nose of the tool.

To load this tool, the nose is opened and the ligature carriage extended to the position shown in FIG. 11. The ligature loop is then mounted on the mounting means 110, the carriage is retracted to the position shown in FIG. 12, and the jaw is closed and locked. In this position the abutment 106 passes through the ligature loop, and the ligature wires pass out of the jaw on either side of the abutment. This tool is used in essentially the same way as the other tools. The loop is placed over the archwire and bracket, the tool is turned 180° to cross the wires, the carriage is drawn back by means of the finger grip to nip the archwire and bracket between the ligature and the abutment, the tool is rotated through a further 120° to twist the ligature wires and seat the archwire into the bracket, the carriage is released, and the shaft is spun until the ligature is sufficiently twisted to be cut.

The dental instruments described are easy to learn and easy to use, even when wearing rubber gloves. The instruments are readily used in confined spaces, such as at the back of a patient's mouth. The ligature wires are twisted from the bracket outwards, the instrument is equally usable right or left handed, and in the embodiments described and illustrated there are few moving paths. In all cases the instruments stretch and tighten the ligature around a bracket before the ligatures are twisted more than 180°, to ensure that full engagement of the archwire occurs in the bracket. During stretching and tightening of the ligature, the abutment on the nose of the instrument braces it against the bracket, so that the bracket is not pulled from the tooth.

In the tool in general, the number of ligature strands that can be twisted together is not limited to two, but preferably separate guide means are provided for each strand.

While the invention has been described with reference to specific elements and combinations of elements, it is envisaged that each element may be combined with any other or any combination of other elements. It is not intended to limit the invention to the particular combinations of elements suggested. Furthermore, the foregoing description is not intended to suggest that any element mentioned is indispensable to the invention, or that alternatives may not be employed. What is defined as the invention should not be construed as limiting the extent of the disclosure of this specification.

I claim:

1. A tool for manipulating a dental ligature to secure an archwire to a bracket on a tooth, said dental ligature having a loop portion and a pair of end portions extending away from said loop portion, said tool comprising:
   a shaft having an end forming an abutment, the dental ligature being positionable, in use, with the loop portion thereof projecting around and beyond said end of the shaft for placement over the archwire and around the bracket;
   a ligature carriage carried by the shaft and secured against rotation relative to said shaft, said carriage being freely longitudinally slidable along said shaft in at least one direction; and
   ligature mounting means on the carriage for receiving the end portions of the dental ligature when the ligature is positioned with the loop portion around and beyond said end of the shaft, said ligature mounting means securing the end portions of the dental ligature to the carriage against movement relative to the carriage;

the ligature carriage being initially longitudinally slidable along the shaft away from said end of the shaft to shorten the loop portion and draw said end of the shaft toward the archwire and bracket, said ligature carriage being thereafter drawn by the ligature toward said end of the shaft, upon subsequent rotation of the entire tool, by the shortening of the loop portion as the ligature is twisted to secure the archwire to the bracket.

2. A tools as claimed in claim 1 in which the shaft is a single axial shaft (ligature carriage is secured against rotation relative to the shaft).

3. A tool as claimed in claim 1 provided with spring means adapted to urge the carriage away from the end of the shaft.

4. A tool as claimed in claim 1 in which the end of the shaft is provided with locating means for guiding the loop portion with respect to the end of the shaft during movement of the carriage.

5. A tool as claimed in claim 4 in which the locating means comprise two channels extending along opposite sides of the end of the shaft, on either side of the abutment formed by said end.

6. A tool as claimed in claim 5 comprising a sleeve on the shaft adjacent the end thereof, the sleeve being alternately movable away from the end to expose the channels at the sides of the end to enable a ligature to be placed in or removed from the channels, and movable towards the end to cover the channels and retain a ligature therein.

7. A tool as claimed in claim 6 in which the sleeve is lockable in position when covering the channels.

8. A tool as claimed in claim 1 in which the shaft is hollow, the end of the shaft is openable, the ligature mounting carriage is carried within the shaft and is movable out of the end when the end is open to permit loading a ligature thereon, and means for moving the carriage is provided externally of the shaft.

9. A tool as claimed in claim 8 in which the openable end comprises a segment thereof hinged to the shaft, and a locking collar is provided on the shaft which is slidable along the shaft to overlie the segment and retain it closed.

10. A tool as claimed in claim 1 in which the ligature mounting means on the carriage comprise an upstanding post, a ramp adjacent the post extending downwardly from the post away from the end of the tool, and clamp means over the ramp movable towards the post whereby to entrap said end portions between the clamp means and the ramp.

11. A tool as claimed in claim 1 in which the shaft is provided with handle means at the end opposite the end forming said abutment.

* * * * *

UNITED STATES PATENT AND TRADEMARK OFFICE
CERTIFICATE OF CORRECTION

PATENT NO. : 4,875,855

DATED : October 24, 1989

INVENTOR(S) : David Beckett

It is certified that error appears in the above-identified patent and that said Letters Patent is hereby corrected as shown below:

Column 7, line 10      delete "tools" and substitute therefor ---tool---

Column 7, lines 11-12      after "shaft" delete "(ligature carriage is secured against rotation relative to the shaft)"

Signed and Sealed this

Thirtieth Day of July, 1991

Attest:

HARRY F. MANBECK, JR.

*Attesting Officer*      *Commissioner of Patents and Trademarks*